United States Patent
Kleffner et al.

(10) Patent No.: US 6,576,875 B1
(45) Date of Patent: Jun. 10, 2003

(54) METHOD AND DEVICE FOR CONTROLLING A TARGETED THERMAL DEPOSITION INTO A MATERIAL

(75) Inventors: Bernard Kleffner, Bliesransbach (DE); Robert Lemor, Saarbrücken (DE)

(73) Assignee: Fraunhofer-Gesellschaft zur Forderung der Angewandten Forschung E. V, Munich (DE)

( * ) Notice: Subject to any disclaimer, the term of this patent is extended or adjusted under 35 U.S.C. 154(b) by 0 days.

(21) Appl. No.: 09/830,491

(22) PCT Filed: Sep. 16, 1999

(86) PCT No.: PCT/EP99/06867
§ 371 (c)(1),
(2), (4) Date: Jul. 26, 2001

(87) PCT Pub. No.: WO00/24468
PCT Pub. Date: May 4, 2000

(30) Foreign Application Priority Data

Oct. 27, 1998 (DE) .......................... 198 49 536
Oct. 27, 1998 (DE) .......................... 198 49 529
Jul. 28, 1999 (DE) .......................... 199 35 455

(51) Int. Cl.⁷ ................................. H05B 1/02
(52) U.S. Cl. ................. 219/494; 219/497; 219/492; 607/102
(58) Field of Search ................. 219/497, 494, 219/706, 492; 604/22; 607/1, 102, 100, 113; 606/32

(56) References Cited

U.S. PATENT DOCUMENTS 4,513,749 A  4/1985  Kino et al.
5,370,121 A  12/1994  Reichenberger
6,299,920 B1 * 10/2001  Saksena ..................... 426/231
6,305,060 B1 * 10/2001  Morris ....................... 600/459
6,379,325 B1 *  4/2002  Benett et al. ................ 604/22

FOREIGN PATENT DOCUMENTS

DE  19506363     8/1996
EP  0 872 262 A  10/1998

OTHER PUBLICATIONS

R. Seip et al: "Noninvasive Real–Time Multipoint Temperature Control for Ultrasoundphased Array Treatments", IEEE Transactions on Ultrasonics, Ferroelectrics and Frequency Control, US, IEEE Inc., New York, vol. 43, No. 6, p. 1063–1072 XP00063975.

R. Seip et al: "Noninvasive Estimation of Tissue Temperature Response to Heating Fields Using Diagnostic Ultrasound", IEEE Transactions on Biomedical Engineering, US, IEEE Inc., New York, vol. 42, No. 8, pp. 828–839 XP000556811 ISSN: 0018–9294.

* cited by examiner

Primary Examiner—Mark Paschall
(74) Attorney, Agent, or Firm—Antonelli, Terry, Stout & Kraus, LLP (57) ABSTRACT

Disclosed is a process for controlling selective application of heat into a material, preferably into a biological material, having an ultrasonic-wave generating unit which couples the ultrasonic waves into the material, an ultrasonic-wave-detecting unit which detects the ultrasonic waves emerging from the material and an evaluation unit which generates information-providing parameters on the basis of the detected ultrasonic waves which provide information about the thermal and structural changes inside the material.

51 Claims, 5 Drawing Sheets

METHOD AND DEVICE FOR CONTROLLING A TARGETED THERMAL DEPOSITION INTO A MATERIAL

TECHNICAL FIELD

The present invention relates to a process and device for controlling selective application of heat into a material, preferably into biological tissue, having an ultrasonic-wave-generating unit which couples ultrasonic waves into the material, an ultrasonic-wave-detecting unit which detects the ultrasonic waves emerging from the material and an evaluation unit which generates information-providing parameters relating to the thermal and structural changes inside the material on the basis of the detected ultrasonic waves.

STATE OF THE ART

Processes of the aforementioned class can be used in material research and material processing in general, in particular with material structures which thermal influence may alter structurally. Of particular interest here are also thermotherapy processes, which are employed in selective hyperthermy of confined areas of tissue, in particular in treating tumors and metastases.

Such types of thermotherapy processes applied today can be divided into two groups:
1. Moderate heating to 43° C. from the outside by means of fields:
   So-called hyperthermy refers to heating regions of tissue inside the body by means of external energy input. It is used in oncology for treating tumors, e.g. to supplement radiation or chemotherapy. Energy input occurs by means of electrical alternating fields or by means of high energy ultrasound. The therapeutically desired increases in temperature are usually about 6° C. above the internal body temperature, which is usually obtained with treatment periods from 20 to 30 minutes.
2. Generating thermal necrosis at temperatures from 45° C. to 200° C. by intracavitary or minimal-invasive processes:
   Confined local thermal tissue damage is a widespread procedure in minimal-invasive surgery and endosurgery in treating pathological changes in tissue, such as tumors and metastases. The most common intracavitary or minimal-invasive methods consist of using infrared-range laser light (LITT: laser-induced thermotherapy), high-frequency coagulator and high-energy ultrasound (HIFU:
   high-intensity focused ultrasound). In these applications, essentially the following tissue reactions occur: solely heating, tissue expansion, denaturation (coagulation), gas bubble formation. Subsequent carbonization is therapeutically undesirable. Examples of the diverse applications are treating liver metastases, mammary carcinoma, prostate tumors and brain tumors. Sometimes, for instance in the treatment of liver metastases, structural damage is achieved by using cold (cryotherapy) or alcohol. In the treatment of the prostrate, hot water may also be applied to the target region instead of laser light or ultrasound.
   In endosurgery in the gastrointestinal tract, laser applicators or HF applicators are utilized, e.g. for esophageal varices or for widening stenoses.

The overall therapeutic goal of these methods of therapy is maximum damage to the malignant tissue while preserving the surrounding benign tissue regions, which may consist of extremely sensitive structures depending on the nature of their function.

A special case is using infrared laser light for treating glaucoma. Glaucoma is the main cause of blindness in the western countries. The end of a laser fiber is placed from the exterior onto the sclera and the chamber-water producing structures below are coagulated (transscleral cyklophoto coagulation). Too high laser temperatures result in undesirable total damage (disruption) of the irradiated ciliar part of the body. With treatment times of two seconds, switching-off criteria for the laser would be of help provided coagulation is good.

Efficiency and further gaining ground of these methods of treatment are therefore closely tied to the availability of a non-invasive procedure, which informs the surgeon in real time about the current therapeutic effect, respectively provides the control parameter or control signals for back coupling to the heat-generating system.

As these effects generally are dependent on the temporal temperature gradients, solely indicating the attained tissue temperature is insufficient for monitoring the therapy. Particularly in view of the individual, tissue-specific and tumor-specific differences, evidence of structural tissue changes is more precise and informative regarding the current, achieved therapeutical effect than the attained tissue temperature.

Hitherto, there are no inexpensive methods of non-invasive or minimal invasive realtime control for these therapy procedures.

Previous approaches at utilizing diagnostic ultrasound for therapy control have aimed solely at giving the attained tissue temperatures. The pertinent literature proposes, i.e., processes to achieve thermometry by measuring the temperature-dependent velocity of sound propagation. See:

Seip. E. S. Ebbini, "Noninvasive Estimation of Tissue Temperature Response to Heating Fields Using Diagnostic Ultrasound," IEEE Trans. Biomed. Eng., vol. 42; August 1995.

Seip, P. VanBaren, C. Simon, E. S. Ebbini, "Non-Invasive Saptio-Temporal Temperature Estimation Using Diagnostic Ultrasound," IEEE Ultrasonics Symposium Proceeding, 1995.

Seip, P. VanBaren, C. A. Cain, E. S. Ebbini, "Noninvasive Real-Time Multipoint Temperature Control for Ultrasound Phased Array Treatments", IEEE Trans. Ultrason., Ferroelect., Freq. Contr., vol. 43, November 1996.

C. Simon, P. VanBaren, E. S. Ebbini, "Quantitative Analysis and Applications of Noninvasive Temperature Estimation Using Diagnostic Ultrasound" IEEE Ultrasonics Symposium Proceeding, October 1997.

C. Simon,. P. VanBaren, E. S. Ebbini, "Two-Dimensional Temperature Estimation Using Diagnostic Ultrasound," IEEE Trans. Ultrason., Ferroelect., Freq.Contr., vol 45, July 1998.

DE 195 06 363 A1 describes a process for non-invasive thermometry in organs under hyperthermic and coagulation conditions. In order to obtain data about structural changes, in this process the to-be-heated tissue is bombarded with ultrasonic waves. The amplitude reflection factor of the tissue is measured in the form of a signal. Then, on the basis of the obtained amplitude reflection factors, the sum is determined from the temperature-dependent and structure-dependent changes in the tissue exposed to the heat.

When applied to thermal material treatment for selective internal structural changes in materials, in general, for example the transition from crystalline to amorphous or a chemical change, there are also no known reliable processes for when and in which regions structural changes occur. The preceding known processes for determining the temperature in the path of the applied thermotherapy and hyperthermy are not suited for precise determination of the structural change and the current spatial extent and of the structural change occurring inside a material.

DESCRIPTION OF THE INVENTION

The present invention improves a process and is a device for controlling selective application of heat into a material, preferably biological tissue, having an ultrasonic-wave-generating unit which couples the ultrasonic waves into the material, an ultrasonic-wave-detecting unit which detects the ultrasonic waves emerging from the material and an evaluation unit which generates information providing parameters for the thermal and structural changes inside the material based on the detected ultrasonic waves, in such a manner that an unequivocal statement can be made about the type and extent of structural change inside the material due to the heat input. Furthermore, the present invention makes possible controlling the heat input into the material in such a manner that the desired goal of the treatment inside the material can be achieved without causing undesired structural changes. Finally the invention is a device for performing this process.

An element of the present invention is a process in which the ultrasonic waves emerging from the material are detected time-resolved and site-resolved, with the detected ultrasonic waves being time-resolved in the evaluation unit and being examined for their change of propagation time relative to the ultrasonic-wave signals stemming from the detected ultrasonic waves which are reflected at the material prior to application of heat and are used as the basis for spatial limitation of the structural changes occurring in the path of the heat input. Based on the objective of the treatment in the material and the determined structural changes in the material, the energy input into the material per time required for the application of heat is controlled.

Contrary to the previous methods in which solely one ultrasonic parameter is proposed for monitoring the temperature, in the process of the invention values are provided with which the structural tissue changes can be measured directly and their temporal formation behavior can be spatially detected.

Therefore, the present invention is based upon utilizing the site-resolved change in the delay time of the backscattered ultrasonic waves to directly determine the structural material change caused in the path of the application of heat. Thus, for example, structural biological tissue irritation can be detected not indirectly, as hitherto, by determining the temperature but by utilizing solely the change in the delay time of the backreflected ultrasonic waves.

In order to be able to detect any changes in the delay time behavior at all, a scale has to first be determined which is obtained at the material to be examined and material to be treated with the application of heat. Therefore, the detected backscattered ultrasonic waves at respectively and the material and their ultrasonic-wave signals are stored accordingly before heat is selectively applied to the material. The measured signals are spectrally detected by means of the detecting unit.

Subsequently, the to-be-treated material is selectively heated, for example by means of introducing laser light locally with the aid of a fiber optical waveguide. However, other methods of selective application of heat are also possible, such as for example exposing the material to external electromagnetic alternating fields or ultrasonic fields, with low-frequency ultrasound being employed for heating and high-frequency diagnostic ultrasound for detection. Another method is deep-freezing using liquid nitrogen.

The application of heat is controllable according to the degree of energy introduced into the material per time unit. Thus, if light is applied, the luminous power can be set accordingly.

For detection and monitoring of the heat input into the material, the backreflected ultrasonic waves are detected during heat input in such a manner that they are detected temporally and simultaneously completely spectrally. The obtained ultrasonic-waves signals are processed time-resolved per transmitted ultrasonic pulse, with in the examination of backreflection ultrasonic-wave signal regions being sought, in which a maximum change in the delay time compared to the scale is observed. On the basis of the measuring geometry, exact information about the location and the expansion of the structural changes inside the material can be derived from the profile of the echo signal. Using this information about the current state inside the material, controlled variables for actuating the heat applying unit can be generated in order to obtain only desired structural material changes. In particular, in treating biological tissue, only those regions of tissue should have sufficient heat applied that are to be selectively destroyed but the respective adjacent tissue regions should be protected from too high heat input.

Furthermore, in combination with the aforedescribed examination using integrated backscattering of the ultrasonic-wave signals received per ultrasonic impulse, a criterion can be obtained in order to be able to detect structural changes in process, for example ranging from the origin and spatial formation of gas bubbles in biological tissue to charring.

Qualitative and quantitative evaluation of the structural change occurring in the material due to heat input can therefore be made by site-resolved measuring of the changes in the delay time of the ultrasonic waves. The changes in the delay time comprise the temperature-dependent velocity of propagation of sound $c(T)$ and with further heating of the naturally diverse thermally induced expansion of the material $\epsilon(T)$. The variable $c(T)$ is used for pure thermometry, for instance for moderate heating and low temperature increases.

Determination of the spatial gradient of the delay time changes along the treated material volume yields the maximum spatial shifts of backscattered ultrasonic signal portions, which are directly connected with the structural change of the material and serve to indicate their spatial expansion.

However, both effects can be separated, on the one hand, on the basis of distinctly strong influences of the macroscopic material expansion reflected in a strong temporal gradient of the delay time changes; on the other hand, in the direction and diverse propagation of the effect away from the origin. Changes in the so-called "integrated backscattering" relative to an output value before heat input or relative to a characterizing, structural material change during heat input are used to control gas formation in the biological tissue to be treated with heat. Subsiding of this effect indicates imminent carbonization of the tissue.

As an alternative to the aforedescribed manner of examining the changes in the delay time of the backreflected ultrasonic waves and their evaluation, changing the acoustic damping coefficient can be used as an information-providing parameter for determining the structural change in a material, preferably into a biological material.

An alternative element of the process of the invention is, therefore, to develop a generic process in such a manner that the ultrasonic waves emerging from the material are detected time-resolved and site-resolved, with the detected ultrasonic waves per ultrasonic pulse being windowed in temporally dynamically adapted time windows in the evaluation unit in such a manner that the beginning part of each time window section has a fixed relationship to the signal course of the detected ultrasonic waves. For each current time window section, a direct or indirect spectral comparison is conducted with at least one time window section of a temporally older ultrasonic-wave pulse which with reference to the temporal signal course has the same beginning part of the section as the current time window section. The terms "direct" and "indirect" indicate the ability to analyze the spectral signal course in the temporal range as well as in the frequency range, ensuring that only those time window sections are compared that also belong to one and the same reflection region inside the to-be-treated material. Using this spectral comparison, an estimation is made of the temporal behavior of the damping coefficient of the material at which the ultrasonic waves corresponding to the detected signals in the individual time window sections are reflected. The temporal behavior of the damping coefficient inside the respective material region to be derived therefrom serves as the basis for a spatial limitation of structural changes occurring inside the material in the path of the heat input. Finally, based on the objective of the treatment in the material and the determined structural changes in the material, heat input per time into the material required for heat application into the material is controlled.

Comparison of a local damping coefficient at various points in time before respectively during heat input for determining a change in the material is only useful if the region for which the damping coefficient is estimated is always the same, i.e. it only need be ensured that in the examination of individual regions of tissue, all the reflected ultrasonic signals that belong to temporally different ultrasonic pulses are compared which also are reflected from the same region of the material.

This is achieved by the reflected signal for determining the local spectra not being provided with a temporally rigid time window, but rather with a dynamic, accompanying time window. Accompanying in the sense that the reflected signal is subdivided into individual sections of the same size, with the beginnings of the sections of each time window always being in a fixed relationship regarding the entire course of the backreflected signal. This accompanying time window can, for example, be determined by the known correlation processes.

Comparison of the spectral information of a signal in an accompanying time window for estimation of the damping coefficient ensures in this manner that the site of the region for which the damping coefficient is estimated is fixed with regard to the material.

Therefore, detection of a change in the damping coefficient is used to determine site-resolved the structural change in the material.

Spectral shifting is used to determine the damping coefficient between two respective time window sections. Due to the frequency dependency of the damping coefficient while passing a damping layer, an ultrasonic signal is weakened in a varying manner in its spectral parts, thereby resulting in shifting the entire spectrum of the signal in the frequency range. This shifting of the spectrum can be determined by various known methods. Determination of the shift can be carried out in the temporal range as well as in the frequency range.

In order to estimate the site-resolved damping coefficient using the spectral shifting method, the reflected ultrasonic signal is divided into individual time window sections, thus temporally time windowed, and the relative shift of the spectra of these time windows relative to each other is observed. From a shift of the spectra relative to each other, the average damping coefficient can be estimated for the region between the respective time windows.

The method of spectral difference is analog except that the damping coefficient is not determined by shifting the spectra but by the variance of the spectra.

To conduct the process of the invention, a device for controlling the selective application of heat into a material, preferably for gentle treatment of biological materials, in particular biological tissue, having an ultrasonic wave generating unit which couples the ultrasonic waves into the material, an ultrasonic wave detecting unit which detects the ultrasonic waves emerging from the material, and an evaluation unit which generates on the basis of the detected ultrasonic waves information-providing parameters which provide information about the thermal and structural changes inside the material, is further improved in such a manner that the ultrasonic-wave-generating unit and the ultrasonic-wave-detecting unit are disposed in the same plane and are jointly adjustable relative to the to-be-treated material, and that a heat-application effecting unit is disposed mainly in the center of the ultrasonic-wave-generating and the ultrasonic-wave-detecting unit and is directed at the material.

Further features can be found in the following description with reference to the accompanying drawings.

BRIEF DESCRIPTION OF THE DRAWINGS

The present invention is made more apparent in the following without the intention of limiting the scope or spirit of the inventive idea using preferred embodiments with reference to the accompanying drawings, showing in.

DESCRIPTION OF THE PREFERRED EMBODIMENTS

Figure 1A:
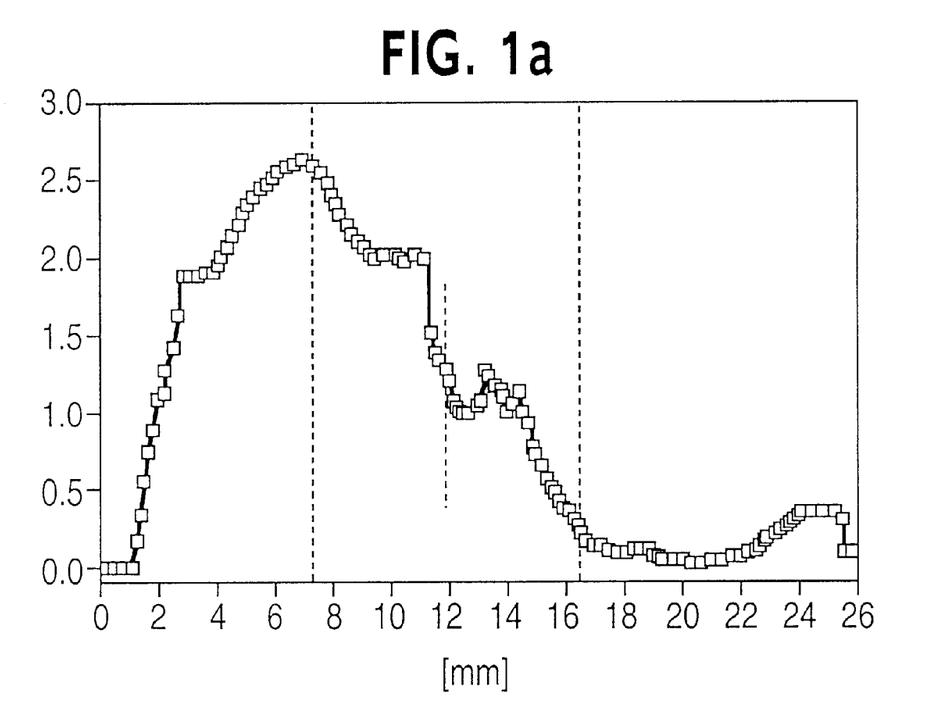
FIGS. 1a and b are a diagram of the delay time shift of a reflected ultrasonic-wave pulse and a photograph of tissue damage due to local heat input.
Figure 1B:
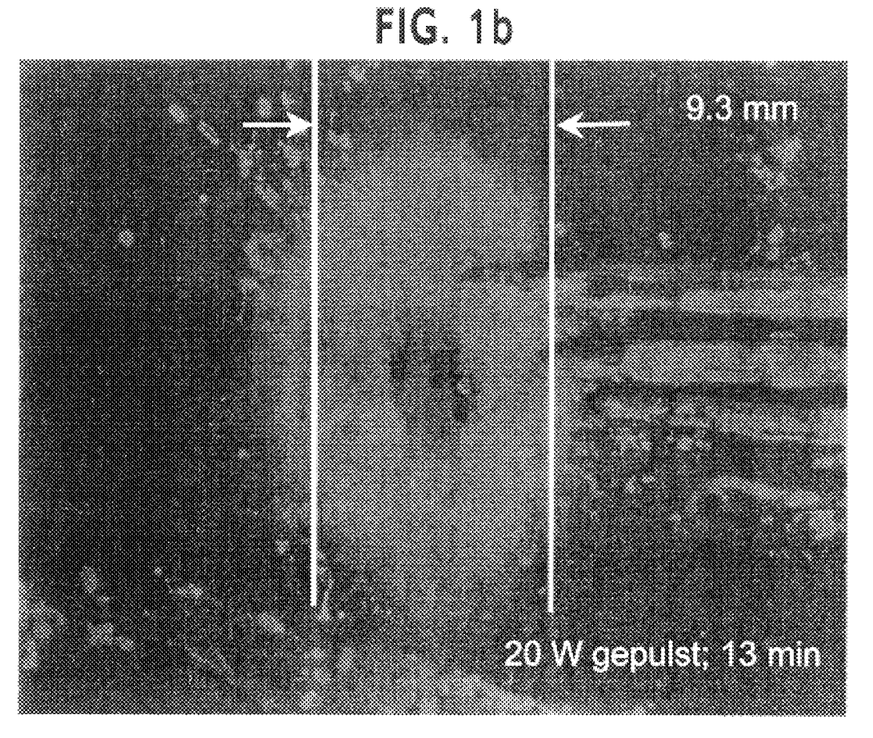

FIG. 1 shows a diagram in which the depth of penetration of an ultrasonic-wave pulse into a material is plotted along the abscissa, in the example of FIGS. 1a and b in biological tissue. The values for the site-resolved delay time shifts for an ultrasonic-wave pulse in $\mu$sec is plotted along the ordinates.

FIG. 1a shows the delay time shift representable per ultrasonic-wave pulse, which is coupled into the biological tissue, relative to the beginning of the course of an ultrasonic pulse detected at normal temperature conditions, i.e. without artificial heat input.

The change in the delay time of an ultrasonic pulse due to of a structural change inside the tissue region as a result of the influence of heat is obtained with the aid of cross correlation of the currently obtained ultrasonic wave signals with the values stored prior to commencing treatment. Thereupon, the obtained curve is evaluated using a polynomial preferably of a lower order, smoothened and evaluated accordingly.

As FIG. 1a shows, in particular, those regions of the curve in which the gradient of the change in the delay time is the greatest is taken into account. This is illustrated by the two vertical boundary lines which simultaneously limit a spatial region of structural changes that were already determined inside the tissue. In FIG. 1b, which is a photograph of the pertinent, heat-treated region of tissue, the light region of tissue corresponds precisely with the region in which structural tissue irritations due to heat input were observed. This region corresponds exactly to the region in which the function in FIG. 1a has the largest gradient. The heat input in FIG. 1b occurs by means of applying light using a fiber optical waveguide which projects from the below into the tissue region in the center of the photograph of FIG. 1b.

In order to draw conclusions about the temperature from the values of the delay time shift, it is necessary to calculate the site-resolved propagation velocities which again form the basis for determining the temperature which are used to control and document the preservation of the healthy tissue.

Figure 2:
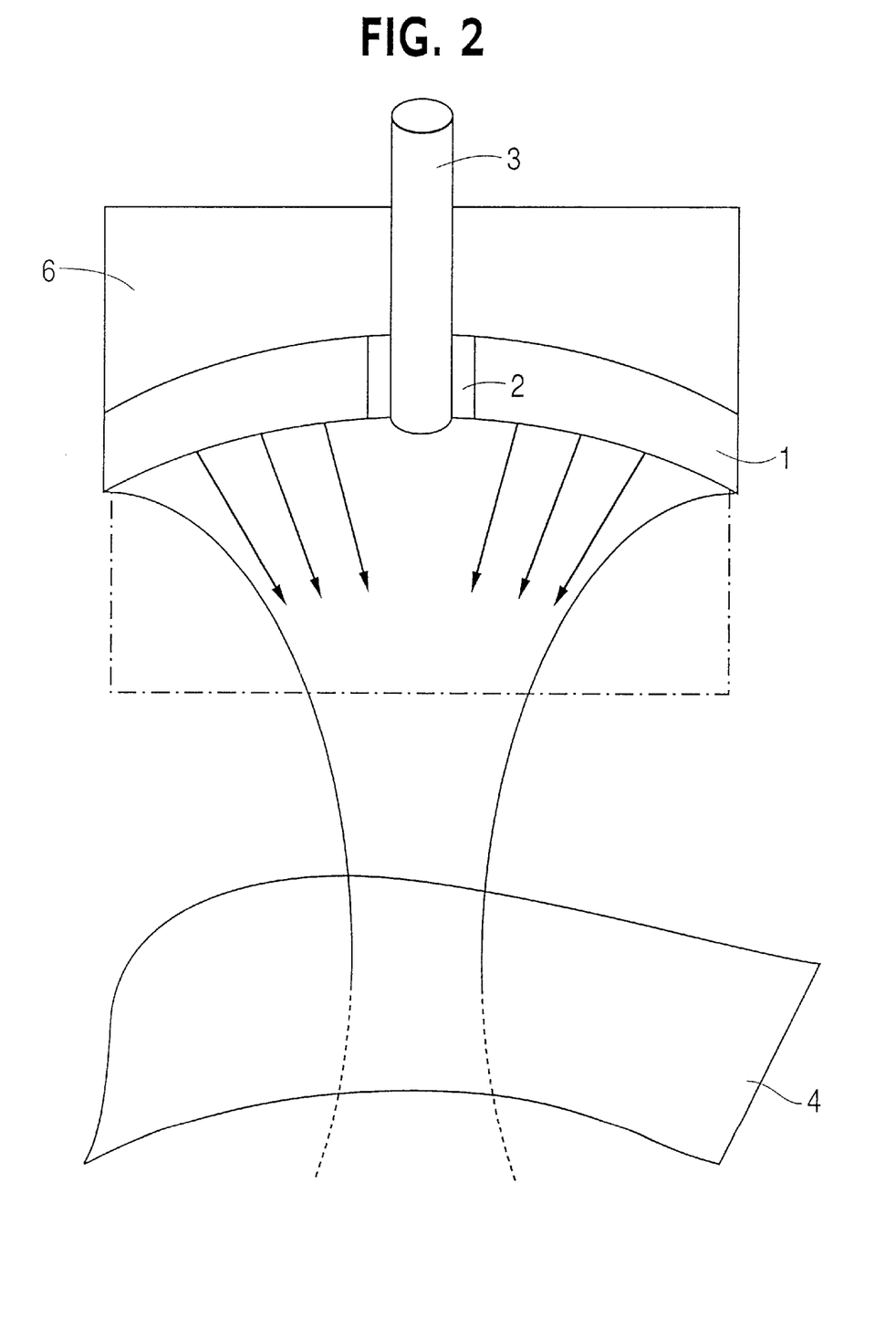
FIG. 2 is a first device for carrying out the process.

FIG. 2 shows a preferred embodiment for carrying out the process of the invention.

An ultrasonic transducer 1 for ultrasound generation and simultaneously for detection is located on a housing part G having a spherically contoured underside. Provided in the center of housing G and ultrasonic transducer 1 is a bore hole through which a fiber optical waveguide 3 is led for selective application of light to the tissue volume 4.

Conventional piercing acoustic heads can be used to ensure unequivocal aiming of the ultrasonic beam at the to-be-treated tissue volume 4. Instead of the provided guiding of the piercing needles, a fiber optical waveguide 3, which can also be replaced by a HF applicator, is suited in the illustrated case.

However, special acoustic transducers are proposed to unequivocally fix the geometric factors which influence the process and therefore must always be taken into account:

Single element transducers, as shown in FIG. 2, which can also be shaped focusing having a central bore hole 2 for receiving the fiber optic waveguide 3 or a high-frequency needle. The coaxial setup ensures the unequivocal aim of the sound beam at the to-be-treated tissue region 4.

Figure 3:
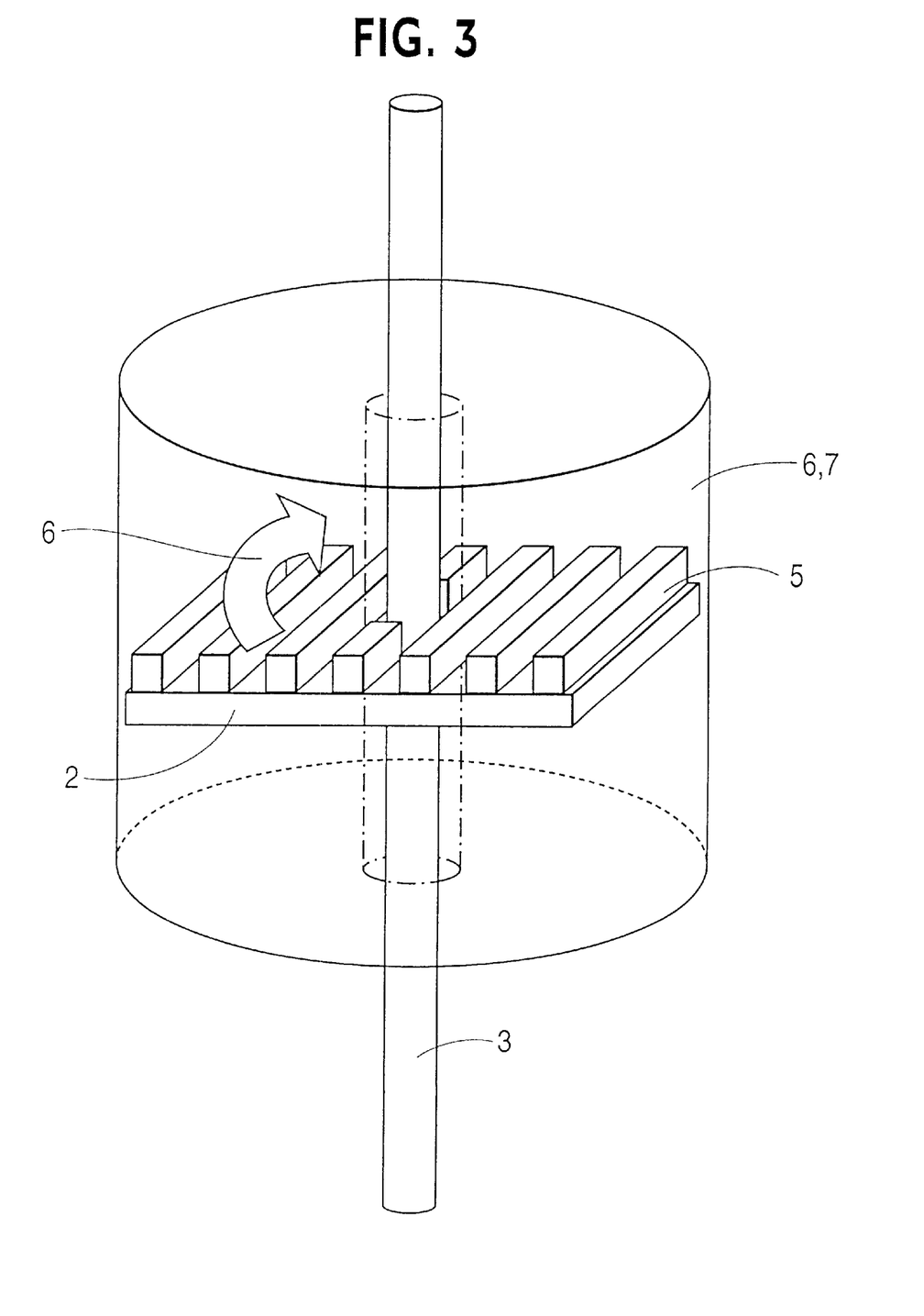
FIG. 3 is a second device for carrying out the process and FIG. 4 is a third device for carrying out the process.

FIG. 3 shows a preferred embodiment having an ultrasonic transducer linear array 5 having a bore hole 2 for receiving heat applicators 3. The array permits achieving electronic depth focusing which aids positioning the applicator, however particularly ensures measuring and representation of the degree and expansion of the therapeutically achieved tissue change. In addition, the array can be disposed in a rotatable manner about the applicator axis 6 inside a housing 7 permitting three-dimensional guidance of the sound beam by means of which detection and representation of the three-dimensional tissue changes occur. In this manner, optimum compensation of three-dimensional movement influences is achieved.

Figure 4:
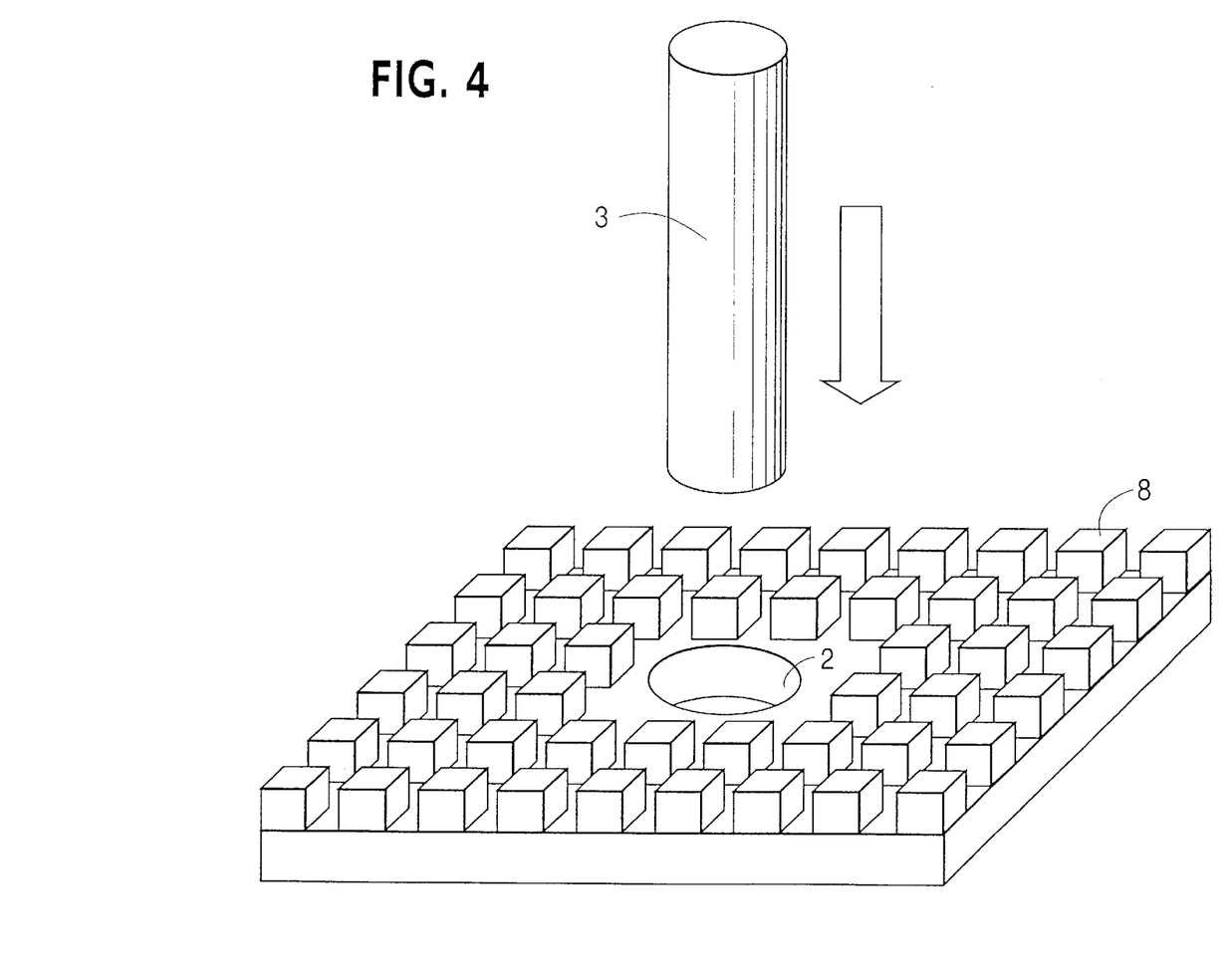

The same can be achieved with a 2D-array 8, as shown in FIG. 4, having a respective bore hole 2 for receiving an applicator 3 and electronic sound field guidance, with the advantage of obviating manual rotation movements. In addition, the fiber optic waveguides or HF applicators can be provided with markers (e.g. made of metal) which are especially easily recognizable for ultrasound.

All the preferred embodiments are sterilizable, respectively can be provided with sterile coats.

List of Reference Numbers 1 ultrasound transducer
2 bore hole
3 fiber optic waveguide
4 tissue region
5 linear transducer array
6 axis of rotation
7 housing
8 single element of a two-dimensional transducer array

What is claimed is:

1. A process for controlling selective application of heat into a material with an ultrasonic wave generating unit which couples ultrasonic waves into the material, an ultrasonic wave detecting unit which detects the ultrasonic waves emerging from the material and an evaluation unit which generates structural and thermal parameters on a basis of the detected ultrasonic waves which provide information about thermal and structural changes inside the material comprising:

detecting ultrasonic waves emerging from the material over a time period of heat treatment;

examining the detected ultrasonic waves from the material to determine a location of structural change in the material caused by the heat treatment at which a maximum delay change in the detected ultrasonic waves occurs; and controlling the application of heat to the location of the structural changes to accomplish a heat treatment plan for the material.

2. The process according to claim 1 wherein:

ultrasonic wave signals produced by the ultrasonic wave detecting unit receiving ultrasonic waves reflected by the material are spectrally determined and integrated over a frequency range of the ultrasonic waves;

a change of an integral of the reflected ultrasonic waves over time beginning from a starting value of the integral obtained before heating of the material is determined; and a parameter about gas bubble formation inside the material based upon the change of the integral is formed.

3. The process according to claim 2, wherein:

the starting value of the integral occurs at the beginning of application of heat at a known temperature and serves as a reference value for detecting changes in the value of the integral.

4. The process according to claim 2 wherein:

after changes in the value of the integral have decreased, obtaining a parameter about imminent carbonization inside the material.

5. The process according to claim 3 wherein:

after changes in the value of the integral have decreased, obtaining a parameter about imminent carbonization inside the material.

6. The process according to claim 1 wherein:

in the evaluation unit, the detected ultrasonic waves of an ultrasonic pulse are dynamically time windowed so that each individual time window is in a fixed relationship to the detected ultrasonic waves;

for each current time window, a spectral comparison is conducted with at least one time window of an earlier ultrasonic-wave which, has a same beginning as the current time window;

from the spectral comparison conducting a time estimation of a damping coefficient of the material for the ultrasonic waves corresponding to detected signals in the time window;

utilizing the time estimation of the damping coefficient to provide a location of structural changes occurring inside the material in a path of the heat input; and based upon a heat treatment plan for the material and the structural changes in the material, controlling an energy input over time into the material which is required to accomplish the heat treatment plan.

7. A process for controlling selective application of heat into a material with an ultrasonic wave generating unit which couples ultrasonic waves into the material, an ultrasonic wave detecting unit which detects the ultrasonic waves emerging from the material and an evaluation unit which generates structural and thermal parameters on a basis of the detected ultrasonic waves which provide information about thermal and structural changes inside the material comprising:

detecting ultrasonic waves emerging from the material;

time windowing the detected ultrasonic waves of an ultrasonic pulse dynamically in the evaluation unit so that each individual time window is in a fixed relationship to the detected ultrasonic waves;

conducting a spectral comparison for each current time window with at least one time window of an earlier ultrasonic wave, which has a same beginning as the current time window;

conducting a time estimation of a damping coefficient of the material for the ultrasonic waves corresponding to detected signals in the time window based on the spectral comparison;

utilizing the time estimation of the damping coefficient to provide a location of structural changes occurring inside the material in a path of the heat input; and controlling the application of heat to the location of the structural changes to accomplish a heat treatment plan for the material.

8. The process according to claim 2 wherein:

in the evaluation unit, the detected ultrasonic waves of an ultrasonic pulse are dynamically time windowed so that each individual time window is in a fixed relationship to the detected ultrasonic waves;

for each current time window, a spectral comparison is conducted with at least one time window of an earlier ultrasonic-wave, which has a same beginning as the current time window;

from the spectral comparison conducting a time estimation of a damping coefficient of the material for the ultrasonic waves corresponding to detected signals in the time window;

utilizing the time estimation of the damping coefficient to provide a location of structural changes occurring inside the material in a path of the heat input; and based upon a heat treatment plan for the material and the structural changes in the material, controlling an energy input over time into the material which is required to accomplish the heat treatment plan.

9. The process according to claim 3 wherein:

in the evaluation unit, the detected ultrasonic waves of an ultrasonic pulse are dynamically time windowed so that each individual time window is in a fixed relationship to the detected ultrasonic waves;

for each current time window, a spectral comparison is conducted with at least one time window of an earlier ultrasonic-wave, which has a same beginning as the current time window;

from the spectral comparison conducting a time estimation of a damping coefficient of the material for the ultrasonic waves corresponding to detected signals in the time window;

utilizing the time estimation of the damping coefficient to provide a location of structural changes occurring inside the material in a path of the heat input; and based upon a heat treatment plan for the material and the structural changes in the material, controlling an energy input over time into the material which is required to accomplish the heat treatment plan.

10. The process according to claim 4 wherein:

in the evaluation unit, the detected ultrasonic waves of an ultrasonic pulse are dynamically time windowed so that each individual time window is in a fixed relationship to the detected ultrasonic waves;

for each current time window, a spectral comparison is conducted with at least one time window of an earlier ultrasonic-wave, which has a same beginning as the current time window;

from the spectral comparison conducting a time estimation of a damping coefficient of the material for the ultrasonic waves corresponding to detected signals in the time window;

utilizing the time estimation of the damping coefficient to provide a location of structural changes occurring inside the material in a path of the heat input; and based upon a heat treatment plan for the material and the structural changes in the material, controlling an energy input over time into the material which is required to accomplish the heat treatment plan.

11. The process according to claim 10 wherein:

in the evaluation unit, the detected ultrasonic waves of an ultrasonic pulse are dynamically time windowed so that each individual time window is in a fixed relationship to the detected ultrasonic waves;

for each current time window, a spectral comparison is conducted with at least one time window of an earlier ultrasonic-wave, which has a same beginning as the current time window;

from the spectral comparison conducting a time estimation of a damping coefficient of the material for the ultrasonic waves corresponding to detected signals in the time window;

utilizing the time estimation of the damping coefficient to provide a location of structural changes occurring inside the material in a path of the heat input; and based upon a heat treatment plan for the material and the structural changes in the material, controlling an energy input over time into the material which is required to accomplish the heat treatment plan.

12. The process according to claim 6, wherein:

the spectral comparison is conducted in one of a time period or a frequency range in response to spectral variance or spectral shift of the detected ultrasonic waves.

13. The process according to claim 7, wherein:

the spectral comparison is conducted in one of a time period or a frequency range in response to spectral variance or spectral shift of the detected ultrasonic waves.

14. The process according to claim 8, wherein:

the spectral comparison is conducted in one of a time period or a frequency range in response to spectral variance or spectral shift of the detected ultrasonic waves.

15. The process according to claim 9, wherein:

the spectral comparison is conducted in one of a time period or a frequency range in response to spectral variance or spectral shift of the detected ultrasonic waves.

16. The process according to claim 10, wherein:

the spectral comparison is conducted in one of a time period or a frequency range in response to spectral variance or spectral shift of the detected ultrasonic waves.

17. The process according to claim 1, wherein:

the ultrasonic wave detecting unit is disposed relative to the material so that only backscattered or back reflected ultrasonic waves are detected.

18. The process according to claim 2, wherein:

the ultrasonic wave detecting unit is disposed relative to the material so that only backscattered or back reflected ultrasonic waves are detected.

19. The process according to claim 3, wherein:

the ultrasonic wave detecting unit is disposed relative to the material so that only backscattered or back reflected ultrasonic waves are detected.

20. The process according to claim 6, wherein:

the ultrasonic-wave-detecting unit is disposed relative to the material so that only backscattered or back reflected ultrasonic waves are detected.

21. The process according to claim 6, wherein:

the ultrasonic wave detecting unit is disposed relative to the material so that only backscattered or back reflected ultrasonic waves are detected.

22. The process according to claim 12, wherein:

the ultrasonic wave detecting unit is disposed relative to the material so that only backscattered or back reflected ultrasonic waves are detected.

23. The process according to claim 1, wherein:

the application of heat inside the material occurs by means of selective application to the material one of electromagnetic radiation, an alternating electrical field or an ultrasonic field.

24. The process according to claim 2, wherein:

the application of heat inside the material occurs by means of selective application to the material one of electromagnetic radiation, an alternating electrical field or an ultrasonic field.

25. The process according to claim 3, wherein:

the application of heat inside the material occurs by means of selective application to the material one of electromagnetic radiation, an alternating electrical field or an ultrasonic field.

26. The process according to claim 4, wherein:

the application of heat inside the material occurs by means of selective application to the material one of electromagnetic radiation, an alternating electrical field or an ultrasonic field.

27. The process according to claim 6, wherein:

the application of heat inside the material occurs by means of selective application to the material one of electromagnetic radiation, an alternating electrical field or an ultrasonic field.

28. The process according to claim 12, wherein:

the application of heat inside the material occurs by means of selective application to the material one of electromagnetic radiation, an alternating electrical field or an ultrasonic field.

29. The process according to claim 17, wherein:

the application of heat inside the material occurs by means of selective application to the material one of electromagnetic radiation, an alternating electrical field or an ultrasonic field.

30. A process in accordance with claim 1 wherein:

a temperature at the location of structural change is determined by resolving a velocity of the ultrasonic waves at the location of the structural change.

31. A device for controlling selective application of heat into a material, comprising:

an ultrasonic wave generating unit which couples ultrasonic waves to the material, an ultrasonic wave detecting unit which detects the ultrasonic waves emerging from the material, an evaluation unit which, based upon the detected ultrasonic waves, generates parameters providing information about thermal and structural changes inside the material and a heat application unit for directing heat to the material; and wherein the ultrasonic wave generating unit and the ultrasonic wave detecting unit are positioned to permit coupling of the ultrasonic waves to and detecting of the ultrasonic waves from a same location within the material and are adjustable relative to the material and the heat application unit, the heat application unit is disposed in a center of the ultrasonic wave generating unit and ultrasonic wave detecting unit, and the ultrasonic wave generating unit and ultrasonic wave detecting unit comprise a two dimensional array.

32. The device according to claim 31:

the ultrasonic wave generating unit and the ultrasonic wave detecting unit are positioned relative to the material so that the ultrasonic waves acting on the material are focused.

33. The device according to claim 31, comprising:

a housing containing the ultrasonic wave generating unit and the ultrasonic wave detecting unit which spaces the units apart and the housing is positionable relative to the material.

34. The device according to claim 32, comprising:

a housing containing the ultrasonic wave generating unit and the ultrasonic wave detecting unit which spaces the units apart and the housing is positionable relative to the material.

35. The device according to claim 31, wherein:

the ultrasonic wave generating unit and the ultrasonic detecting unit are rotatable about an axis of rotation which coincides with the axis of the heat application unit.

36. The device according to claim 32 wherein:

the ultrasonic wave generating unit and the ultrasonic detecting unit are rotatable about an axis of rotation which coincides with the axis of the heat application unit.

37. The device according to claim 33, wherein:

the ultrasonic wave generating unit and the ultrasonic detecting unit are rotatable about an axis of rotation which coincides with the axis of the heat application unit.

38. The device according to claim 34, wherein:

the ultrasonic wave generating unit and the ultrasonic detecting unit are rotatable about an axis of rotation which coincides with the axis of the heat application unit.

39. The device according to claim 31, wherein:

the heat application unit is a glass fiber which guides light into the material.

40. The device according to claim 32, wherein:

the heat application unit is a glass fiber which guides light into the material.

41. The device according to claim 33, wherein:
the heat application unit is a glass fiber which guides light into the material.

42. The device according to claim 35, wherein:
the heat application unit is a glass fiber which guides light into the material.

43. The device according to claim 31, wherein:
the heat application unit is a diagnostic ultrasonic device which generates a temperature increase inside a tissue region.

44. The device according to claim 32, wherein:
the heat application unit is a diagnostic ultrasonic device which generates a temperature increase inside a tissue region.

45. The device according to claim 33, wherein:
the heat application unit is a diagnostic ultrasonic device which generates a temperature increase inside a tissue region.

46. The device according to claim 35, wherein:
the heat application unit is a diagnostic ultrasonic device which generates a temperature increase inside a tissue region.

47. The device according to claim 39, wherein:
the heat application unit is a diagnostic ultrasonic device which generates a temperature increase inside a tissue region.

48. A device for controlling selective application of heat into a material, comprising:
an ultrasonic wave generating unit which couples ultrasonic waves to the material, an ultrasonic wave detecting unit which detects the ultrasonic waves emerging from the material, an evaluation unit which, based upon the detected ultrasonic waves, generates parameters providing information about thermal and structural changes inside the material and a heat application unit for directing heat to the material; and wherein the ultrasonic wave generating unit and the ultrasonic wave detecting unit are positioned to permit coupling of the ultrasonic waves to and detecting of the ultrasonic waves from a same location within the material and are adjustable relative to the material and the heat application unit, the heat application unit is disposed in a center of the ultrasonic wave generating unit and ultrasonic wave detecting unit, and the ultrasonic wave generating unit and ultrasonic wave detecting unit comprise a one dimensional array.

49. The device of claim 48 wherein:
the ultrasonic wave generating unit and the ultrasonic detecting unit are rotatable about an axis of rotation which coincides with the axis of the heat application unit.

50. The device of claim 48 wherein:
the heat application unit is a glass fiber which guides light into the material.

51. The device of claim 48 wherein:
the heat application unit is a diagnostic ultrasonic device which generates a temperature increase inside a tissue region.

* * * * *